United States Patent [19]

Eichel et al.

[11] 4,024,237

[45] May 17, 1977

[54] NOVEL COMPOSITIONS FOR ESTABLISHING ENVIRONMENTAL CONDITIONS FAVORABLE TO ORAL LEUCOCYTES

[76] Inventors: Bertram Eichel, 30 Ashmont Drive, Framingham, Mass. 01701; Vincent F. Lisanti, 32 Woodcliff Ave., North Bergen, N.J. 07047

[22] Filed: Aug. 4, 1975

[21] Appl. No.: 601,849

[52] U.S. Cl. .................................... 424/49; 424/53; 424/54; 424/183

[51] Int. Cl.[2] ...................... A61K 7/16; A61K 7/20; A61K 7/24

[58] Field of Search ................. 424/49, 53, 54, 183

[56] References Cited

UNITED STATES PATENTS

| | | | |
|---|---|---|---|
| 2,025,655 | 12/1935 | Faunce | 424/49 |
| 2,042,359 | 5/1936 | Putt | 424/49 |
| 2,779,708 | 1/1957 | Russell et al. | 424/49 |
| 3,232,833 | 2/1966 | Riviere | 424/183 |
| 3,506,642 | 4/1970 | Koh et al. | 424/183 |
| 3,510,561 | 5/1970 | Koh | 424/183 |
| 3,651,207 | 3/1972 | Lauster et al. | 424/54 |
| 3,839,590 | 10/1974 | Battista | 424/49 |

*Primary Examiner*—Sam Rosen

[57] ABSTRACT

Novel compositions for establishing environmental conditions in the human oral cavity for maintaining healthy, functional oral leucocytes, said compositions comprising a non-toxic mixture of effective amounts of: (1) at least one compound for maintaining a colloidal and viscous environment within the oral cavity which favors and promotes oral leucocyte locomotion, phagocytosis and bacterial kill; (2) at least one compound providing and maintaining a balanced ionic environment which favors and promotes locomotion, phagocytosis and bacterial kill; (3) at least one compound providing a source of energy for said oral leucocytes; and (4) at least one compound for maintaining substantially a physiological pH to promote leucocyte functions while avoiding other tissue and cell injury; and novel products and processes employing the same.

9 Claims, No Drawings

NOVEL COMPOSITIONS FOR ESTABLISHING ENVIRONMENTAL CONDITIONS FAVORABLE TO ORAL LEUCOCYTES

BACKGROUND OF THE INVENTION

Leucocytes (inflammatory cells) elaborated in the gingival sulcus, present in the oral cavity and/or on the surface of oral tissues play a major, and possible the primary role in the natural host defense system for preventing infection and various oral diseases and malfunctions resulting from the presence of microorganisms and their toxins in the oral cavity and/or from the presence of bacteria in the oral cavity. Ninety-nine percent of these inflammatory cells are polymorphonuclear neutrophils (PMN).

A study of 18 human subjects (male and female, ranging in age from 15 to 60, each having at least 20 teeth) illustrates the order of magnitude of this first line of body defense. Oral lavages were collected from each subject by chewing paraffin for thirty seconds in the presence of a physiologically compatible fluid environment. This yielded ubiquitous PMN of host oral origin ranging from 5 million to 33 million per ml. of hose fluid (saliva, gingival exudate, etc.) contribution contained in such lavages. For a more detailed and informative basis for these findings, see, for example, our prior publications: *Journal of Dental Research*, Vol. 40, 1961, p. 747; *Journal of the American Society of Periodontists*, Vol. 1, No. 3, May/June, 1963, pp. 109–117; *Archives of Oral Biology*, Vol. 9, 1964, pp. 299–314; *Journal of Society of Cosmetic Chemistry*, Vol. 15, 1964, pp. 149–154; *Dental Abstracts*, October, 1964, p. 651; *Annals New York Academy of Science*, Vol. 131, Art. 2, 1965, pp. 812–814 and 851–867; *Science*, Vol. 166, pp. 1424–1428; and *Archives of Oral Biology*, Vol. 18, 1973, pp. 505–516, all of which are incorporated by reference herein.

The advantages, if not the necessity, for keeping these leucocytes healthy, e.g., viable, active, locomoting, phagocytizing and capable of killing bacteria will be readily apparent. It will be equally as apparent that, where possible, one must avoid hinderance of these vital body defense cells and their mechanisms so as not adversely to affect maintenance of their normal healthy functional state.

The ideal condition in humans is for these oral leucocytes to remain and to be maintained in a healthy, viable state so as to be able to perform their function as a prime body defense mechanism. In other words, the normal and optimum condition is for these oral leucocytes to exist in that state nature intended.

Thus, for example, as reported in *Archives of Oral Biology*, Vol. 9, 1964, pp. 299–314, and *Science*, Vol, 166, 1969, pp. 1424–1428, it has been consistently observed that properly prepared oral lavages obtained from healthy humans contain large number of peripheral-wandering oral leucocytes which are intact, alive and functional. In such typical harvests, many of the leucocytes, free or contained in clusters, locomote, vigorously extend pseudopodia, exhibit protoplasmic flow, cell stretching and movement of cell organelles internally. These leucocytes also frequently phagocytize (actively engulf) large rod, chain, filamentous, or other microorganisms. (These important functions of these essential cells of the body defense system have been recorded dramatically by us in time laspe motion picture films.)

While this is the healthy state, humans in general in most instances do not maintain environmental conditions in the oral cavity favoring healthy, viable ubiquitous leucocytes. Thus, due to such factors as the ingestion or oral application of substances or complexes of substances which are nonphysiological in nature, i.e., substances which nature did not intend humans to ingest or be exposed to such as conventional toothpastes and mouth washes, tobacco smoke, high concentration alcoholic beverages, etc., which factors are in general peculiar to civilized humans as distinguished from other members of the animal kingdom, the environment of these Leucocytes is so altered as to interfere with their normal, healthy function, and, in turn, their body defense role.

By way of illustration, oral lavages sampled from healthy individuals with protective leucocyte lavage solution-toothpaste extracts, or with protective leucocyte lavage solution-mouthwash extracts (the tooth pasted and mouthwashes having been purchased over the counter at drugstores), or with non-protective leucocyte lavage solutions have been observed to contain damaged, fragmenting and fragmented leucocytes. By way of further illustration, oral lavages collected with protective leucocyte solutions from healthy individuals after smoking one cigarette without inhaling contain, after harvesting, isolated leucocytes and clusters of leucocytes which: (1) appear to verge on the brink of locomotion and possibly phagocytosis, but remain incapable of overcoming the locomotion and phagocytosis-inhibiting effect provided by their environment; (2) at the periphery and within some of the clusters are rounded and their granules exhibit active brownian motion, one example of damaged leucocytes; (3) vigorously form blebs or vesicles (bubble blowing), other examples of toxicity, while they may attempt to locomote very sluggishly and also attempt feeble phagocytosis without success; (4) are obviously injured to the point where they are inert or fragmented. Many of these observations, which are perhaps lacking in drama when observed under the microscope, also have been recorded in time lapse photomicrography motion pictures. Such sequences, in fact, are visually quite boring as distinguished from those sequences of the activities of viable, healthy leucocytes. The respective effects can be observed experimentally for some hours after the environmental condition has been established.

Since the role in body defense played by ubiquitous leucocytes (such as those present in the oral cavity) has heretofore been well known, it was apparent that any inhibition, even a partial inhibition, of the functioning of these leucocytes for periods of time, would be detrimental to the health of the host individual and may, in fact, be a prime cause of diseases in the oral cavity and elsewhere. From what has been stated, it should also be apparent that any non-toxic, edible and digestible compositions which can be safely taken within and applied to the tissues of the oral cavity and which are capable of maintaining the proper environmental conditions which favor continuous functioning of oral leucocytes in the manner nature intended are inherently of considerable usefulness.

It is to such compositions and the maintenance of healthy functional leucocytes to which this invention is directed.

SUMMARY OF THE INVENTION

According to the present invention, novel prophylactic and therapeutic compositions are provided for obtaining and/or maintaining proper environmental conditions within the oral cavity for metabolizing, healthy, viable (e.g., resting, locomoting or phagocytizing) oral leucocytes. We have discovered that novel compositions are useful in the prophylaxis, treatment and cure of oral disease such as that commonly treated by periodontists.

The novel compositions of this invention comprise non-toxic ingredients which favor and promote leucocyte function, including locomotion, phagocytosis and protoplasmic function resulting in the control and kill of bacteria. Consequently, oral diseases such as periodontal disease and perhaps also dental caries, which have been associated with infective factors by those skilled in the art can be controlled and even successfully treated, especially early periodontal disease such as marginal gingivitis (commonly known as "bleeding gums").

More specifically, the compositions of this invention contain at least effective amounts of a non-toxic ingestible mixture of ingredients for: (1) maintaining a colloidal and viscous environment within the oral cavity which favors and promotes oral leucocyte locomotion, phagocytosis and bacterial kill; (2) providing the oral leucocytes with a suitable source of energy when needed; (3) providing and maintaining a balanced ionic environment which favors and promotes locomotion, phagocytosis and bacterial kill; and (4) maintaining substantially a physiological pH in order to promote leucocyte functions while avoiding other tissue and cell injury.

As was mentioned previously, the present invention is directed to novel compositions for establishing environmental conditions within the oral cavity favoring and/or maintaining healthy, functional, viable oral polymorphonuclear neutrophils, a prime host defense cell against invasion of foreign bodies such as bacteria through the oral cavity.

A primary object of this invention, therefore, is to provide novel compositions of the foregoing description, which compositions may be applied topically and eaten, if desired.

Another object is to provide novel products and processes utilizing these prophylactic and therapeutic compositions.

Other objects of the invention will in part be obvious and will in part appear hereinafter.

For a fuller understanding of the nature and objects of the invention, reference should be had to the following detailed disclosure.

The novel prophylactic compositions of this invention, when applied topically within the oral cavity provide the proper environmental conditions for viable, healthy, functional ubiquitous leucocytes of host origin contained therewithin. Under optimum conditions, e.g., balanced diet and taking of foodstuffs, no smoking, no imbibing of alcoholic beverages, no use of conventional toothpastes or mouthwashes, etc., nature may provide within the oral cavity the proper environmental condition for maintaining the integrity of the oral leucocyte. Yet, we have repeatedly observed by microscopic examination that sedimentable harvests obtained from oral fluids, for example whole saliva, from healthy humans yield non-functional or injured leucocytes, often few in number, with frequent evidence of fragmenting or fragmented leucocytes. Subsequent sedimentable harvests collected from the same subjects at random but in the presence of corrective prophylactic lavage compositions as described in this invention are necessary to provide the environment required by these leucocytes for their proper function with respect to protoplasmic flow, cell stretching, locomotion, pseudopodia formation, and finally phagocytosis and kill of microorganisms.

We have discovered that the necessary environmental conditions are established and/or maintained by applying topically a composition containing at least effective amounts of a non-toxic mixture of ingredients for: (1) maintaining a colloidal and viscous environment of the oral cavity which favors and promotes oral leucocyte locomotion, phagocytosis and bacterial kill; (2) providing the oral leucocytes with a suitable source of energy, when needed; (3) providing and maintaining a balanced ionic environment which favors and promotes locomotion, phagocytosis and bacterial kill; and (4) maintaining the pH substantially the same as in the oral cavity, e.g., 5.5 to 9.0, but preferably as close to physiological pH as possible. The composition may, but not necessarily, also contain non-toxic ingredients for providing a negative charge potential in the oral cavity to reduce clustering of leucocytes and to eliminate agglutination and precipitation of protoplasmic particles.

As examples of useful reagents for maintaining the requisite colloidal and viscous environment, mention may be made of the dextrans, especially those having molecular weights ranging from between 15,000 to 40,000,000, perferably those from about 60,000 to 90,000; cellulose ethers such as carboxymethyl cellulose and hydroxyethyl cellulose; polyvinylpyrrolidone; gelatin, etc.

As examples of energy-providing reagents, mention may be made of carbohydrates such as glucose, sucrose, and fructose; phosphorylated sugar intermediates such as glucose-6-phosphate, fructose-6-phosphate non-phosphorylated sugar intermediates such as salts, preferably alkali metal salts (e.g., sodium, potassium or lithium salts) of pyruvic, lactic, acetic acid, or citric acid, etc., and metabolizable fats and proteins.

As examples of useful reagents for providing a properly balanced ionic environment, mention may be made of inorganic salts such as sodium chloride, potassium chloride, calcium chloride, magnesium chloride; magnesium sulfate; monopotassium dihydrogen phosphate, monosodium dihydrogen phosphate, dipotassium monohydrogen phosphate, disodium monohydrogen phosphate; sodium bicarbonate, etc.

As examples of reagents for maintaining the pH within the desired range, mention may be made of phosphate buffers, $CO_2$-bicarbonate buffer, tris buffers, glycylglycine buffer, etc., the $CO_2$-bicarbonate buffer being preferred.

As examples of useful ingredients for providing a negative charge potential, mention may be made of heparin, chondroitin sulfate; and other polyanionic polysaccharides.

The novel compositions of this invention may also contain therapeutic concentrations of fluoride proven to be of value as an anti-caries agent and non-therapeutic reagents performing specifically desired functions, e.g., flavoring ingredients; combination flavoring and effervescing ingredients, e.g., citric acid, tartaric acid, etc.; preservatives to increase shelf life, e.g., antioxidants, colorants, viscous reagents, solvents, etc.

The effective amounts of the above mentioned four classes of ingredients may be readily determined empirically by those skilled in the art by sampling the formulation and then examining under the microscope (e.g., in the manner to be described hereinafter) leucocytes taken from the oral cavity to determine if they are viable, being capable of healthy protoplasmic flow, locomotion and phagocytosis and bacterial kill after application of the composition. By simple and routine analysis, necessary adjustments in the formulation may be made to achieve optimum results.

In such a manner, we have determined the preferred ranges of ingredients set forth in the following table, it being appreciated that beneficial results may also be obtained by employing lesser or greater amounts than those recited.

TABLE

| Ingredient | Wt./100cc Aqueous Solution |
|---|---|
| 1. | 0.50 to 10.0 g. |
| 2. | 0.10 to 3.0 g. |
| 3. | 0.26 to 5.2 g. |
| 4. | 0.015 to 1.5 g. |

The prophylactic composition may be formulated for application in a variety of ways. The only criticality is that, regardless of the manner of formulation, the effective ingredients must be capable of remaining in solution in the fluid environment of the mouth. Thus, the novel prophylactic compositions of this invention may be formulated in a dry or substantially dry from, e.g., as a powder, capsule, tablet, lozenge, etc., as a paste, or as a rinse or mouthwash by forming a mixture of the composition in water or in a suitable water-miscible organic solvent, or a mixture of solvents.

The following are illustrative of typical formulations of the novel prophylactic compositions of this invention.

Formulation 1

A powder was prepared by grinding thoroughly a mixture of the following ingredients:

| | | |
|---|---|---|
| Dextran (clinical grade, m.w. 60–90,000) | 5.0 | gm. |
| Glucose | 0.5 | gm. |
| Sodium Chloride | 1.4 | gm. |
| Sodium Bicarbonate | 0.5 | gm. |
| Heparin | 0.01 | gm. |

Formulation 2

A powder was prepared by grinding thoroughly a mixture of the following ingredients:

| | |
|---|---|
| Dextran | 2.5000 gm. |
| Glucose | 0.5000 to 1.0000 gm. |
| Sodium Chloride | 1.0420 gm. |
| Heparin | 0.0050 gm. |
| Calcium Chloride | 0.0152 gm. |
| Potassium Chloride | 0.0175 gm. |
| Monopotassium Dihydrogen Phosphate | 0.0080 gm. |
| Magnesium Sulphate . $7H_2O$ | 0.0073 gm. |
| Disodium Monohydrogen Phosphate | 0.0705 gm. |

Formulation 3

A powder was prepared by grinding thoroughly a mixture of the following ingredients:

| | |
|---|---|
| Dextran | 2.5000 gm. |
| Glucose | 0.5000 to 1.0000 gm. |
| Sodium Chloride | 1.0420 gm. |
| Sodium Bicarbonate | 0.7660 gm. |
| Heparin | 0.0050 gm. |
| Calcium Chloride | 0.0152 gm. |
| Potassium Chloride | 0.0175 gm. |
| Monopotassium Dihydrogen Phosphate | 0.0080 gm. |
| Magnesium Sulphate . $7H_2O$ | 0.0073 gm. |

Formulation 4

A powder was prepared by grinding thoroughly a mixture of the following ingredients:

| | |
|---|---|
| Dextran (clinical grade, m.w. 60–90,000) | 8.500 gm. |
| D-Glucose | 1.695 gm. |
| Sodium Chloride | 2.373 gm. |
| Sodium Bicarbonate | 7.743 gm. |
| Calcium Chloride | 0.047 gm. |
| Potassium Chloride | 0.061 gm. |
| Monopotassium Dihydrogen Phosphate | 0.029 gm. |
| Magnesium Sulphate . $7H_2O$ | 0.051 gm. |
| L(+) Tartaric Acid | 0.652 gm. |

Dry formulations such as those given above may be employed in the dry state, e.g., as a powder mixed with water to make a slurry for brushing the teeth and massaging the gums, or as a powder or a tablet which is dissolved directly in the mouth. They may also be dissolved in an appropriate volume of water or a non-toxic water-miscible solvent to provide a solution useful for brushing or as a mouthwash. They may also be incorporated into a toothpaste. Finally, they may be formulated into a chewing gum or lozenge in order to dissolve into the mouth more slowly and thereby provide the desired protective conditions for longer and more continuous intervals of time.

For optimum effectiveness, the prophylactic compositions of this invention, e.g., the compositions disclosed in the foregoing illustrative examples, should be retained in solution in the oral cavity for at least thirty and preferably at least sixty seconds. Since the compositions are completely non-toxic, they need not be expectorated, but may be swallowed except for chewing gum formulations. This important aspect of the invention permits the prophylactic compositions to be employed at any time, e.g., in restaurants, or any other public place and/or while the individual is in transit. It will be apparent that, when employing dry mixtures or toothpastes, time is required for the composition to dissolve, whereas the mouthwashes or dry formulations dissolved in an appropriate amount of water initiate action as soon as they are taken in the mouth.

For optimum effectiveness, treatment should be repeated at least upon arising, after eating, smoking, drinking high concentration alcoholic beverages, and before going to sleep. An important feature of the present invention is that the compositions are completely non-toxic and, hence, may be taken appreciably more often, if desired. It will be appreciated that lesser than optimum treatment will provide benefits accordingly.

The following examples further show by way of illustration and not by way of limitation the utility and reduction to practice of this invention.

EXAMPLE 1

Typical human whole saliva harvests were obtained from healthy individuals by introducing chewing paraffin into the mouth of the subject who then chewed without swallowing and expectorated the fluid harvests into a graduated centrifuge tube. Dextran containing solutions (see formulations above) were then added to the centrifuge tube. Ref., see *Archives of Oral Biology*, Vol. 9, 1964, pp. 299–314. The whole saliva harvests were then centrifuged at 1,000–1,300 xg for 5 to 10 minutes. A drop of the sedimented harvest and accompanying salivary fluid was mounted on a slide, a cover slip was placed thereover and sealed with paraffin, and the slide was then placed under a Zeiss phase contrast microscope with the magnification set at about 450x. or 1,250x. The sediments containing sloughed epithelial cells, granular masses, relatively sparse numbers of leucocytes in various stages of degeneration, microorganisms and mammalian cell fragments (mostly of leucocyte origin).

These observations were recorded on film. Leucocytes in fluid-cell harvests in repeated tests, using different subjects, were observed to be in substantially the same nonfunctional, degenerating and degenerated state.

EXAMPLE 2

5.0 ml. of an aqueous solution of the prophylactic composition of formulation 3 was introduced into the mouths of the subjects along with the chewing paraffin. After centrifugation, a drop of sediment along with its fluid environment was mounted on a slide and placed under the phase contrast microscope. (In instances where time lapse photographs were obtained, the taking of the photographs was started as soon as possible (usually 5 to 10 minutes), after the slide was placed under the microscope. The sequences were photographed at 2-second intervals, exposure time being 0.5 second. Showing the resulting film at 16 frames per second yielded an impression of events 40 times faster than they occur as viewed by the observer through the microscope. The average time utilized for specific sequences varied from one to four hours. Each entire sequence was projected and examined in 90 to 360 seconds.) In every instance, the leucocytes contained in the sediment were observed to be intact and functional.

Relatively few mammalian cell fragments were present in most instances. Since the results were substantially reproducible in subject after subject, the ability of the formulation to provide the requisite environment for oral leucocyte function was essentially established.

The following relates to studies we undertook to demonstrate that those conditions which encourage phagocytosis by peripheral PMN obtained from the human oral cavity also enhance the numbers of oral PMN which exhibit intense endogenous nitro-blue tetrazolium (NBT)-reduction and, therefore, bacterial kill.

In order to appreciate fully the nature and significance of this study and its relevancy to this invention, a few brief introductory comments are perhaps advisable. Millions of polymorphonuclear neutrophils (PMN) can be harvested in their functional state by employing a suitable, balanced physiological medium in any individual human oral cavity containing a reasonable complement of teeth. It has previously been reported that when phosphate buffer, pH 7.4, was employed as an oral lavage, a small portion of these PMN exhibited intense endogenous reducing reaction employing NBT as the disclosing agent, a phenomenon which was correlated with the production of sufficient amounts of endogenous hydrogen peroxide within these cells during in vivo phagocytosis. It has also been disclosed that a marked increase in the endogenous NBT-reducing capacity of these cells occurred in the presence of critical concentrations of added exogenous hydrogen peroxide. It is well known that hydrogen peroxide is formed in PMN during phagocytosis and that a 2 to 4-fold increase of hydrogen peroxide is shown following phagocytosis by PMN. It has previously been reported that the rate of endogenous reduction of NBT in normal peripheral blood PMN is stimulated by phagocytosis in vitro, while peripheral blood PMN from patients with chronic granulomatous disease (CGD) fail to reduce NBT. A direct correlation between endogenous NBT-reduction and bacterial kill capability by PMN has previously been demonstrated. It has also been previously observed that the number of peripheral blood PMN that yield NBT-positive endogenous reaction increased in individuals with systemic bacterial infection.

EXAMPLE 3

Procedure: PMN was harvested from the oral cavities of three systemically healthy humans in known manner by using a protective leucocyte medium (PLM) omitting D glucose as the oral lavage. One half of each PLM oral lavage studied was used to observe PMN function under the phase contrast microscope. The other half of each PLM lavage was allowed to stand in siliconized tubes in a constant temperature bath at 37° C for 15 minutes to enhance phagocytosis by the PMN. To compare the rate of endogenous-NBT-reduction between resting PMN and cells whose metabolic activity had been stimulated by in vitro phagocytosis, 1 ml. aliquots of the oral lavage was taken before (zero time) and after 15 minutes incubation. The supernatant components present in the oral lavages were removed by centrifuging at 1000 xg for 3 minutes at room temperature. The sediments were washed twice and finally resuspended in 2.0 ml. of isotonic 0.1M $KH_2PO_4 \cdot Na_aHPO_4$ buffer, pH 7.4 ($PO_4$ buffer). The entire procedure from the instant of introducing the lavage into the oral cavity and the resuspension of the sediment in phosphate buffer took 5 minutes. Accordingly, the zero time incubated sample aged five minutes at room temperature, permitting some phagocytic activity, and the 15-minute incubated sample also aged another five minutes, allowing a 20-minute period for phagocytosis. After the addition of 1.0 ml. of 0.1% NBT (dissolved in phosphate buffer) to each sample, the reaction tubes were placed in a constant temperature bath and incubated at 37° C for 45 minutes to allow the endogenous reduction of NBT to occur. To establish appropriate controls, the general procedure was repeated for each subject by using isotonic 0.1M phosphate buffer, pH 7.4 as the oral lavage. In each instance, the NBT reactions took place in phosphate buffer in the absence of added substrate. The influence of sodium cyanide at final concentrations of 0.001M upon the NBT-reduction system was also determined. At the end of the 45-minute NBT incubation period, the reactions were stopped and wet preparations were made for bright field microscopy examination in known manner. Differential counts were per-formed upon each specimen based on the number of intensely reactive PMN as opposed to non-reacticve or virtually non-reactive cells. At least 200 PMN were counted on each slide. Observations: In the presence of PLM with and without glucose as lavages in these subjects, PMN under the phase contrast microscope always exhibited functional activities including phagocytosis. When isotonic 0.1M phosphate buffer with or without glucose was used as the oral lavage, morphological integrity of the PMN was observed, but phagocytic and functional activity of the PMN were not observed. Some of the PMN revealed intense reduction of NBT evidenced by the production of large amounts of deep purple formazan deposits (NBT-positive PMN). The percentage of these NBT-positive cells varied depending upon the nature of the lavage medium, the capacity of the latter to permit phagocytosis, and the incubation period for phagocytic activity. Since D-glucose did not alter the number of the NBT-positive PMN compared to those lavages in which D-glucose was omitted, the NBT-positive PMN solely reflected the amount of endogenous reducing activity. The ranges and means of the percent endogenous-NBT-positive PMN for the three subjects is summarized in the following table.

30-minute incubation phagocytosis periods of PLM lavages in vitro yielded only slight increases in the extent of the intense endogenous-NBT-reducing reaction observed for the 20-minute period. The inability of cyanide to inhibit any of these intense endogenous-NBT-reducing reactions in oral PMN confirms the previously reported observation that this metabolic system is cyanide insensitive.

A previous report in the literature compared healthy and agranulomatous diseased patients and found that intense endogenous-NBT-reducing reaction in peripheral blood PMN was correlated with bacterial kill activity by these cells. It can be concluded that the intense endogenous-NBT-reducing reaction evident in oral PMN and described above not only is directly correlated with the phagocytic capability of these host defense cells in systemically healthy subjects, but also is a measure of the capacity for the oral PMN to kill bacteria.

Another previously reported study showed values for intense endogenous-NBT-reudcing reactions in blood PMN equal to 8.5% for healthy individuals, 5.8 to 9.5% for patients with non-bacterial diseases (including viral) and 29.0 to 47.0% for 54 patients with bacterial illnesses (notably meningitis). One patient with a gingival abcess showed an intense endogenous-NBT-positive blood PMN response. It was concluded that the elevated endogenous-NBT-reduction was related in each instance to increased in vivo phagocytosis. These results also closely parallel the findings of the above experiments relating to in vitro phagocytosis by oral PMN.

Table I

Effect of Phagocytosis upon the Extent of Endogenous-NBT-Reducing Reactions in Human Oral PMN

| Lavage Medium | Incubation Time for Phagocytosis | Mean (and range) of NBT-positive PMN Subject 1 | Subject 2 | Subject 3 |
|---|---|---|---|---|
| | | % | % | % |
| $PO_4$ Buffer | 5 minutes | 11.0(3.0–13.0) | 9.0(6.0–12.0) | 10.3(9.0–12.0) |
| | 20 minutes | 11.6(9.0–14.0) | 9.4(3.0–11.0) | 11.0(10.0–12.0) |
| PLM | 5 minutes | 21.2(19.0–24.0) | 21.6(18.0–24.0) | 22.0(20.0–23.0) |
| | 20 minutes | 42.2(40.0–45.0) | 41.2(39.0–43.0) | 42.7(41.0–44.0) |

After allowing five minutes incubation for phagocytosis to occur for the phosphate buffer lavages, the mean number of endogenous-NBT-positive cells did not exceed 11.0%. On the other hand, as shown in Table I, 5 minutes incubation in the PLM lavage medium elevated the mean endogenous-NBT-positive PMN from 9.0–11.0% to 21.2–22.0%. Following the 20-minute phagocytosis incubation period, the mean yield of endogenous-NBT-positive cells was not altered when the phosphate buffer oral lavage was employed. In contrast, the mean endogenous-NBT-positive cell yield increased to 41.2–42.7% for the PLM oral lavage. Sodium cyanide (0.001M) did not alter the NBT-reaction of the PMN in any of these experiments.

The importance of the results of the foregoing experiments will be readily apparent to those skilled in the art.

The base-line (9.0–11.6%) intense endogenous-NBT-reducing reaction for the phosphate buffer lavages reflects the extent of on-going in vivo phagocytosis which probably occurs in the gingival sulcus (the probable source of the PMN) and its immediate vicinity in the oral cavity at the instant the lavage is introduced into the mouth. Since PMN function, especially phagocytic activity, was observed in every case in PLM-lavages as opposed to the absence of function in every case when the phosphate buffer lavages were employed, the correlation between the occurrence of in vitro phagocytic activity and the increased intense endogenous-NBT-reducing reaction in the PMN (21.2–22.0% after 5 minutes and 41.2–42.7% after 20 minutes) has been established. In other experiments, It will, therefore, be most apparent that the intense endogenous-NBT-reducing activities of oral PMN constitute a measure of an important host cell defense system within the oral cavity. It can serve as a useful indirect phagocytic and/or bacterial kill index for the further investigation of local and systemic bacterial disorders.

The following relates to a clinical study of the efficacy of a novel composition of this invention in the treatment of periodontal disease.

EXAMPLE 4

Fifteen adults were selected having severe to very severe gingivitis. The composition of Formulation 4 was provided to each subject in the dry state in amounts sufficient to last 6 weeks. Each subject was told to discontinue the use of his usual toothpaste and/or the mouthwash, whatever they were. Instead, they were instructed to apply the toothbrush moistened with water to a portion (approximately 500 mg.) of the dry leucocyte-protective powder to make a slurry for brushing the teeth and to dissolve approximately 600 to 900 mg. of the dry formulation in 10 ml. of water for application to the oral tissues as a mouthwash. The mouth was not to be rinsed after the use of the toothbrush and mouthwash. If possible, the subject was told to repeat this treatment four times daily: (1) after breakfast; (2) after lunch; (3) after dinner or supper; and (4) before going to bed. If four applications could not be made daily, the subject was told to reduce them to three and not less than twice daily. In the latter case, the subject was to use the formulation after breakfast and before going to bed. Otherwise, they were instructed to continue their usual daily oral habits of eating, smoking, etc. Prior to the study, each subject was examined by a dentist and the severity of gingivitis was scored as follows: very severe-4; severe-3; moderate-2; slight-1; none-0. At the end of the 6-week period, the subjects were re-examined to determine the improvement, if any, in their gingivitis. This study showed dramatic results. At the end of the six-week treatment period, 14 of the 15 subjects showed marked clinical improvement of the disease state as follows: six subjects showed total disappearance (0) of gingivitis; one improved from very severe (4) to slight (1); two improved from severe (3) to slight (1); four subjects improved from severe (3) to moderate (2); and one from very severe (4) to moderate (2). One showed no improvement, although it is not known whether he followed the prescribed routine.

This clinical study is believed by us to be the first reported demonstration of a dramatic improvement of gingivitis by the mere routine topical application by the subject of any formulation. Of great significance is the fact that the subjects treated themselves in accordance with their own routines and without treatment or visits to a dentist or other professional.

It is to be noted that periodontal diseases are characterized by inflammation of the gingivae (gums), alveolar bone, periodontal membrane and cementum, often associated with progressive degeneration of these tissues. The sequence of events with or without bone involvement frequently proceeds as follows: inflammatory enlargement of the soft tissue (the gingivae) resulting in the formation of the fundamental lesion called the periodontal pocket, which in effect causes an increase in the size and depth of the gingival crevice around the neck of the tooth beyond the range of normalcy. Thus, we find in gingivitis, the earliest phase of periodontal disease, that the gingivae exhibit inflammation, swelling, change in contour, bleeding, change in texture and often give off a purulent or puss or discharge from newly formed gingival pockets. Those sequela of gingivities which involve the loss of supporting bone for the teeth due to the inflammatory process are called periodontitis or pyorrhea. Various degrees of loss of the supporting bone or osseous tissues, pocket formation and mobility of the teeth occur. Mobility of the teeth is a late finding in the disease and usually results in the loss of the teeth.

It is very difficult to discriminate between the contribution of local factors vs. systemic factors in individuals with periodontal disease, especially in apparently systemically healthy people. However, it has been suspect for a long period of time that oral microbial flora are in some way significantly associated with periodontal disease, yet no specific or exact role has been defined for any of the microbial flora as an etiological factor. It is noteworthy that histopathological examination of the inflamed gingivae, especially that portion of the tissue adjacent to the gingival pocket, exhibits a wide variety of inflammatory cells or leucocytes: for examples, granulocytes, especially polymorphonuclear neutrophils; lymphocytes; monocytes; macrophages or histiocytes; mast cells, etc.

Our findings are consistent with the view that microorganisms and their toxins are ever-present foreign bodies or invaders in the oral cavity and constitute a constant threat or inciting agent relating to the occurrence of lesions in the teeth (dental caries) and lesions of the gums (periodontal disease, the earliest manifestation of which is gingivitis). We regard the microorganisms and their toxins as a stimulus or stress to which the host responds by mobilizing its defense mechanisms, both cellular and acellular. Examples of host defense cells are leucocytes, such as polymorphonuclear neutrophils, lymphocytes, etc. Free enzymes, such as myeloperoxidase and lysozyme produced by polymorphonuclear neutrophils, immunoglobulins, etc. are examples of acellular host defense mechanisms.

Numerous polymorphonuclear neutrophils capable of phagocytizing and killing oral microorganisms can be harvested from lavages of any human oral cavity when teeth and, therefore, the gingivae are present. These host defense cells can be obtained in the millions in any lavage from individuals with healthy gingivae indicating that the body constantly maintains this primary line of defense at all times. The numbers of these cells obtained increase considerably from individuals with gingivitis or other symptoms of periodontal disease. We, therefore, view the microorganism-toxin stimulus and host defense system response as an equilibrium which, when disturbed in favor of the microorganism-toxin stimulus, results in disease. Conversely, when conditions favor the host defense system response, control of the microorganism-toxin stimulus and maintenance of the healthy tissue states are realized. It follows when disease manifestations occur in the oral tissues (such as gingivitis, periodontitis, etc. in the absence of systemic disease), restoration of conditions which favor the host defense system response (such as microorganism phagocytosis, bacterial kill, and toxin detoxification by leucocytes) should reverse the tendency toward the continued insidious progression of disease, either by cessation of the degenerative processes taking place, or by restoring the healthy state.

Since certain changes may be made in the above products and processes without departing from the scope of the invention herein involved, it is intended that all matter contained in the above description shall be interpreted as illustrative and not in a limiting sense.

We claim:

1. A composition for establishing environmental conditions in the human oral cavity for maintaining healthy functional oral leucocytes, said composition comprising a non-toxic mixture of effective amounts of: (1) at least one compound selected from the group consisting of dextran, cellulose ethers, polyvinylpyrrolidone and gelatin for maintaining a colloidal and viscous environment within the oral cavity which favors and promotes oral leucocyte locomotion, phagocytosis and bacterial kill; (2) at least one compound selected from the group consisting of carbohydrates, fats and proteins to provide a source of energy for said oral leucocytes; (3) an inorganic salt providing and maintaining a balanced ionic environment which favors and promotes locomotion, phagocytosis and bacterial kill; and (4) at least one compound selected from the group consisting of phosphate buffers, carbon dioxide-bicarbonate buffers, tris buffers and glycylglycine buffers for maintaining substantially a physiological pH to promote leucocyte functions while avoiding other tissue and cell injury.

2. A composition as defined in claim 1 wherein said pH is from about 5.5 to about 9.

3. A composition as defined in claim 1 including at least one additional reagent selected from the group consisting of anti-caries agents, flavoring agents, effervescing agents, preservatives, colorants, viscous reagents and solvents.

4. A composition as defined in claim 1 wherein said first mentioned compound is present in an amount of from 0.5 to 10.0 parts by weight; said second mentioned compound in from 0.1 to 3.0 parts by weight; said third mentioned compound in from 0.26 to 5.2 parts by weight; and said last mentioned compound in from 0.015 to 1.5 parts by weight.

5. A solution, toothpaste or powder comprising a composition as defined in claim 1.

6. A composition as defined in claim 4 wherein said compound providing a colloidal and viscous environment is dextran; said compound providing a source of energy is glucose; said balanced ionic environment is provided by a mixture of compounds comprising sodium chloride, sodium bicarbonate, calcium chloride, potassium chloride, monopotassium dihydrogen phosphate and magnesium sulfate; and said physiological pH is provided by the interaction of sodium bicarbonate and tartaric or citric acid.

7. A process which comprises applying orally a composition as defined in claim 1.

8. A process as defined in claim 7 wherein said composition is applied as a solution, slurry, powder or as a toothpaste.

9. A composition as defined in claim 1 including at least one compound selected from the group consisting of heparin, chondroitin sulfate and polyanionic polysaccharides to provide a negative charge potential whereby to reduce clustering of leucocytes and to eliminate agglutination and precipitation of protoplasmic particles.

* * * * *